(12) United States Patent
Gingrich et al.

(10) Patent No.: US 7,311,674 B2
(45) Date of Patent: Dec. 25, 2007

(54) END EFFECTOR ASSEMBLY CAP AND TISSUE REMOVAL DEVICE AND RELATED METHODS

(75) Inventors: Jon Gingrich, Shrewsbury, MA (US); Malka Berndt, Lexington, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 300 days.

(21) Appl. No.: 10/876,613

(22) Filed: Jun. 28, 2004

(65) Prior Publication Data

US 2006/0009711 A1  Jan. 12, 2006

(51) Int. Cl.
*A61B 10/00* (2006.01)
(52) U.S. Cl. .................................... 600/564
(58) Field of Classification Search .............. 600/562, 600/564, 127, 128, 129; 606/39, 167, 205, 606/206, 207, 208, 209, 223, 108; 206/305
See application file for complete search history.

(56) References Cited

U.S. PATENT DOCUMENTS

| | | | | |
|---|---|---|---|---|
| 5,228,451 A * | 7/1993 | Bales et al. | ................. | 600/564 |
| 5,403,342 A * | 4/1995 | Tovey et al. | ................ | 606/205 |
| 5,545,169 A * | 8/1996 | Yarger | ........................ | 606/108 |
| 5,613,499 A * | 3/1997 | Palmer et al. | ............... | 600/564 |
| 5,681,348 A * | 10/1997 | Sato | ........................... | 606/205 |
| 5,702,080 A * | 12/1997 | Whittier et al. | ........... | 248/205.5 |
| 5,722,422 A * | 3/1998 | Palmer et al. | ............... | 600/564 |
| 5,810,876 A * | 9/1998 | Kelleher | ...................... | 606/205 |
| 5,820,630 A * | 10/1998 | Lind | ........................... | 606/208 |
| 5,843,121 A * | 12/1998 | Yoon | .......................... | 606/206 |
| 6,099,550 A * | 8/2000 | Yoon | .......................... | 606/205 |
| 6,139,508 A * | 10/2000 | Simpson et al. | ............ | 600/564 |
| 6,142,956 A * | 11/2000 | Kortenbach et al. | ........ | 600/564 |
| 6,149,607 A * | 11/2000 | Simpson et al. | ............ | 600/567 |
| 6,273,860 B1 * | 8/2001 | Kostylev et al. | ............ | 600/564 |
| 6,352,503 B1 * | 3/2002 | Matsui et al. | ............... | 600/104 |
| 6,425,901 B1 * | 7/2002 | Zhu et al. | .................... | 606/142 |
| 6,514,197 B1 * | 2/2003 | Ouchi et al. | ................. | 600/106 |
| 6,514,269 B2 * | 2/2003 | Yamamoto | .................. | 606/170 |
| 6,527,753 B2 * | 3/2003 | Sekine et al. | ............... | 604/264 |
| 6,599,309 B1 * | 7/2003 | Gilman | ........................ | 606/205 |
| 6,689,122 B2 * | 2/2004 | Yamamoto | ...................... | 606/1 |
| 6,699,180 B2 * | 3/2004 | Kobayashi | .................. | 600/127 |
| 6,866,668 B2 * | 3/2005 | Giannetti et al. | ............. | 606/99 |
| 2003/0195432 A1 * | 10/2003 | Kortenbach et al. | ........ | 600/562 |
| 2004/0097958 A1 * | 5/2004 | Whittman et al. | .......... | 606/108 |
| 2004/0230097 A1 * | 11/2004 | Stefanchik et al. | ......... | 600/127 |
| 2005/0049520 A1 * | 3/2005 | Nakao | ........................ | 600/562 |
| 2005/0070959 A1 * | 3/2005 | Cichocki, Jr. | ............... | 606/223 |

* cited by examiner

*Primary Examiner*—Max F. Hindenburg
*Assistant Examiner*—Fangemonique Smith
(74) *Attorney, Agent, or Firm*—Finnegan, Henderson, Farabow, Garrett and Dunner, LLP

(57) ABSTRACT

Embodiments of the invention include a cap for a medical device. The cap includes a body defining a cavity configured to accommodate at least a portion of an end effector assembly of the medical device, and a tissue removal portion attached to the body and configured to remove a tissue sample disposed within the end effector assembly when the cavity is not accommodating the end effector assembly. Embodiments of the invention also may include a medical kit including a medical device and a cap and a method of performing a medical procedure with the cap.

19 Claims, 10 Drawing Sheets

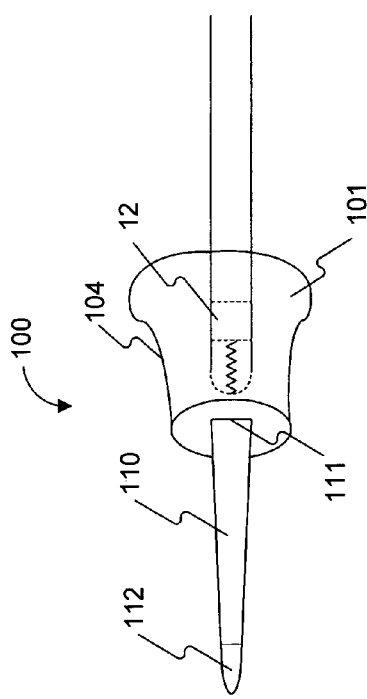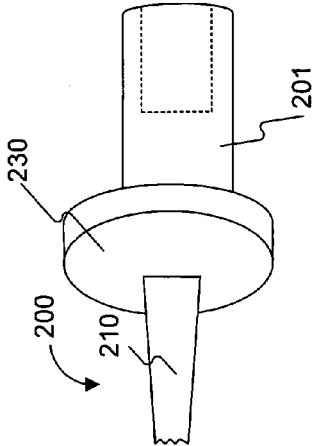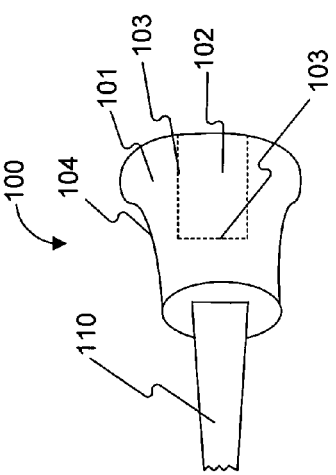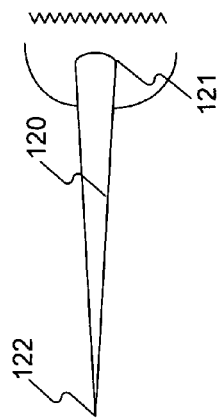

END EFFECTOR ASSEMBLY CAP AND TISSUE REMOVAL DEVICE AND RELATED METHODS

FIELD OF THE INVENTION

Embodiments of the invention include a cap for a medical device. The cap includes a body defining a cavity configured to accommodate at least a portion of an end effector assembly of the medical device, and a tissue removal portion attached to the body and configured to remove a tissue sample disposed within the end effector assembly when the cavity is not accommodating the end effector assembly. Embodiments of the invention also may include a medical kit including a medical device and a cap.

BACKGROUND OF THE INVENTION

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member for insertion into a lumen of an endoscope. The tubular member is sufficiently long and flexible to follow a long, winding path of the body cavity. An end effector assembly, such as a biopsy forceps assembly, is attached at a distal end of the tubular member, and a handle is attached at a proximal end of the tubular member. The handle may be configured to actuate the end effector assembly.

In methods of using the biopsy forceps device, an endoscope is placed in a patient's body cavity adjacent to a tissue site from which the acquisition of a tissue sample is desired. The biopsy forceps device is then advanced to the tissue site via a working channel of the endoscope. Once the biopsy forceps device is next to the portion of the tissue from which the acquisition of a tissue sample is desired, the jaws of the biopsy forceps assembly are opened. The open jaws are then advanced to the tissue site, and then the jaws are closed. The closing of the jaws causes a tissue sample to be lodged in the end effector assembly. The biopsy forceps device is then removed from the body cavity via the working channel of the endoscope.

Once removed from the working channel of the endoscope, the jaws may be opened to remove the tissue sample. However, tissue sometimes has a tendency to stick within the jaws, and thus makes it difficult for the user to remove the tissue for further processing. One method of removing a tissue sample is to briskly move the jaws back and forth in formalin so as to cause the tissue to fall into the formalin. The device may then be rinsed and placed back into the body cavity to acquire another tissue sample. This process may be repeated dozens of time for certain disease protocols. Formalin, however, is a known cancer causing substance, and therefore not suited to be placed in the body.

Another method to remove tissue from the jaws is to use common items such as toothpicks or medical syringe type needles to pick the tissue out of the jaws. However, the use of such items to remove the tissue may damage the tissue and render the tissue unsuitable for further processing. Moreover, such items probably are not sterile.

Packaging of an endoscopic medical device, and particular biopsy forceps devices, also presents various issues. Because the handle is rigid, the tubular member is flexible, and both have sealed internal components, there is not as much of a need to protect these portions of the biopsy forceps device. The end effector assembly, however, and particularly the jaws, have more sensitive, intricate, portions (e.g., sharpened portions of the teeth) that are not sealed and thus may be more easily damaged if mishandled and/or not properly protected during shipping. One method of protecting the end effector assembly is by placing a portion of a flexible catheter or a rubber-like sock having a length of about 0.5 inches to 3 inches over the end effector assembly. While the material used is minimal and inexpensive and is easy to implement, the user may sometimes forget to remove the catheter tubing or sock prior to placing the end effector assembly through the working channel of the endoscope, and thus the catheter tubing or sock may become lodged in the working channel.

SUMMARY OF THE INVENTION

In accordance with the invention, an embodiment of the invention includes a cap for a medical device. The cap includes a body defining a cavity configured to accommodate at least a portion of an end effector assembly of the medical device, and a tissue removal portion attached to the body and configured to remove a tissue sample disposed within the end effector assembly when the cavity is not accommodating the end effector assembly.

Another embodiment of the invention includes a medical kit. The medical kit includes a medical device having a handle portion, an end effector assembly, and an elongate member connecting the handle portion to the end effector assembly. The medical kit also includes a cap for the medical device. The cap includes a body defining a cavity configured to accommodate at least a portion of the end effector assembly of the medical device, and a tissue removal portion attached to the body and configured to remove a tissue sample disposed within the end effector assembly when the cavity is not accommodating the end effector assembly.

Various embodiments of the invention may include any or all of the following features. The tissue removal portion may be a shaft. The shaft may be tapered to a tip. The body may include a concave outer surface. At least a portion of the cap may be made of an elastomeric material. A protrusion may radially extend beyond an outermost radial portion of the body and the tissue removal portion. The protrusion may be a disk. The protrusion may have a greater cross-sectional area than the body. A protrusion may be configured to prevent the cap from advancing through a working channel of an endoscope. The tissue removal portion may be integrally formed with the body. The end effector assembly may be a jaw assembly. The medical device may be a endoscopic biopsy forceps. The cavity may be configured to receive the at least a portion of the end effector assembly when the end effector assembly is in a closed configuration. At least a portion of the end effector assembly may be disposed in the cavity. The tissue removal portion may be configured to scoop tissue out of the end effector assembly. The tissue removal portion may include a concave inner surface. The tissue removal portion may be configured to extend alongside the end effector assembly when the cavity is accommodating the end effector assembly. The tissue removal portion may extend from an end of the body that defines an opening of the cavity. The tissue removal portion may expand from a first end of the body opposite a second end of the body that defines an opening of the cavity.

A further embodiment of the invention includes a method of packaging a portion of a medical device. The method includes providing a medical device including a handle portion, an end effector assembly, and an elongate member connecting the handle portion to the end effector assembly, providing a cap including a body defining a cavity configured to accommodate at least a portion of the end effector assembly of the medical device, and a tissue removal portion attached to the body and configured to remove a tissue sample disposed within the end effector assembly when the cavity is not accommodating the end effector assembly, and placing the at least a portion of the end effector assembly within the cavity.

Yet another embodiment of the invention includes a method of performing a medical procedure. The method includes providing a medical device including a handle portion, an end effector assembly, and an elongate member connecting the handle portion to the end effector assembly, providing a cap including a body defining a cavity configured to accommodate at least a portion of the end effector assembly of the medical device, and a tissue removal portion attached to the body and configured to remove a tissue sample disposed within the end effector assembly when the cavity is not accommodating the end effector assembly, at least a portion of the end effector assembly being disposed in the cavity, removing the cap from the at least a portion of the end effector assembly, obtaining tissue with the end effector assembly, and removing tissue from the end effector assembly with the tissue removal portion.

Various embodiments of the invention may include any or all of the following features. The end effector assembly may be a jaw assembly. The medical device may be an endoscopic biopsy forceps. At least a portion of the end effector assembly when the end effector assembly is placed within the cavity may be in a closed configuration. The tissue removal portion may be a shaft. The shaft may be tapered to a tip. The body may include a concave outer surface. At least a portion of the cap may be made of an elastomeric material. A protrusion may radially extend beyond an outermost radial portion of the body and the tissue removal portion. The protrusion may be a disk. The protrusion may have a greater cross-sectional area than the body. A protrusion may be configured to prevent the cap from advancing through a working channel of an endoscope. The tissue removal portion may be integrally formed with the body. The tissue removal portion may be configured to scoop tissue out of the end effector assembly. The tissue removal portion may include a concave inner surface. The tissue removal portion may be configured to extend alongside the end effector assembly when the cavity is accommodating the end effector assembly. The tissue removal portion may extend from an end of the body that defines an opening of the cavity. The tissue removal portion may expand from a first end of the body opposite a second end of the body that defines an opening of the cavity. Placing the tissue removal portion alongside one of the end effector assembly and the elongate member. Scooping tissue out of the end effector assembly with the tissue removal portion.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 3 is a schematic view of a protective cap covering the end effector assembly of a medical device according to an embodiment of the present invention.

FIG. 4 is a schematic view of a portion of the protective cap of FIG. 3.

FIG. 5 is a schematic view of a portion of a protective cap according to another embodiment of the present invention.

FIG. 6 is a schematic view of a portion of a protective cap according to a further embodiment of the present invention.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1:
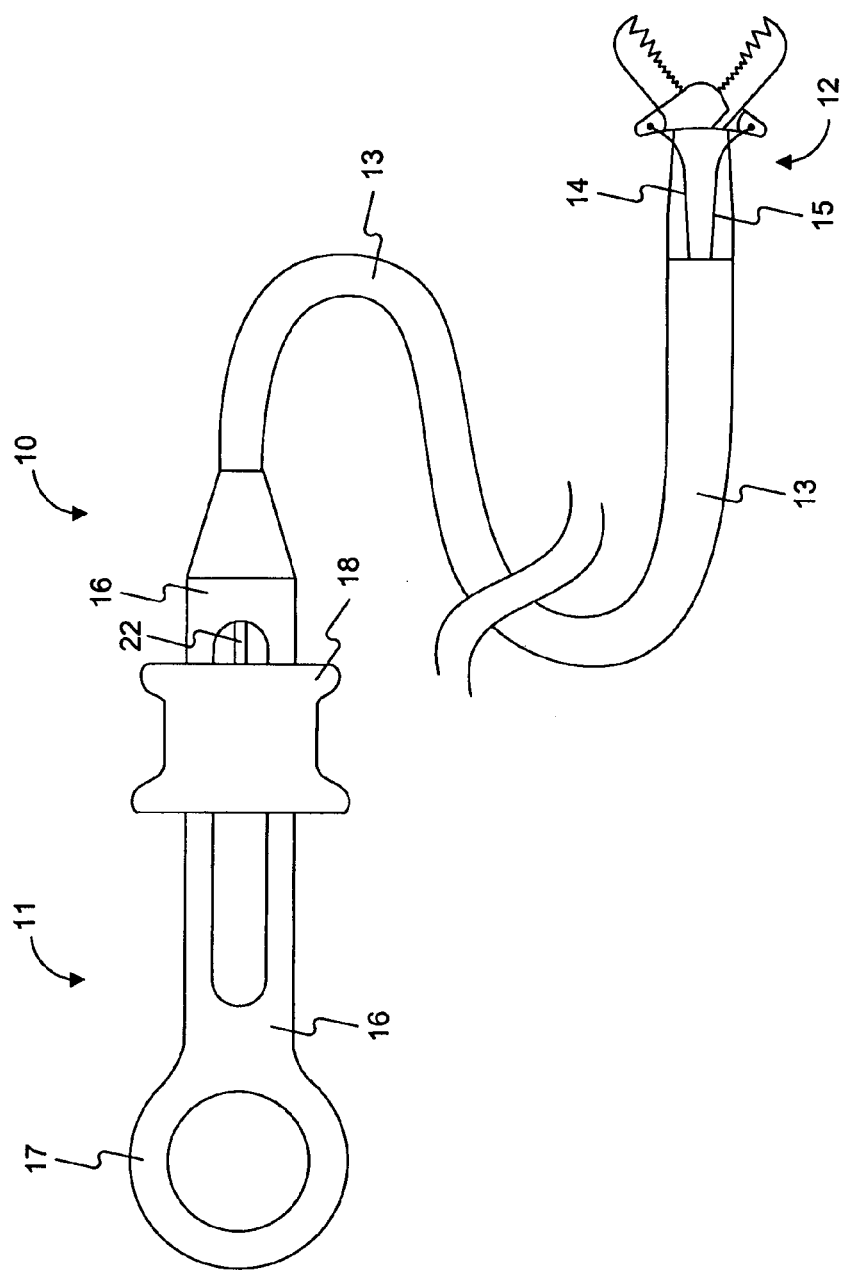
FIG. 1 is a schematic view of a medical device.
Figure 2:
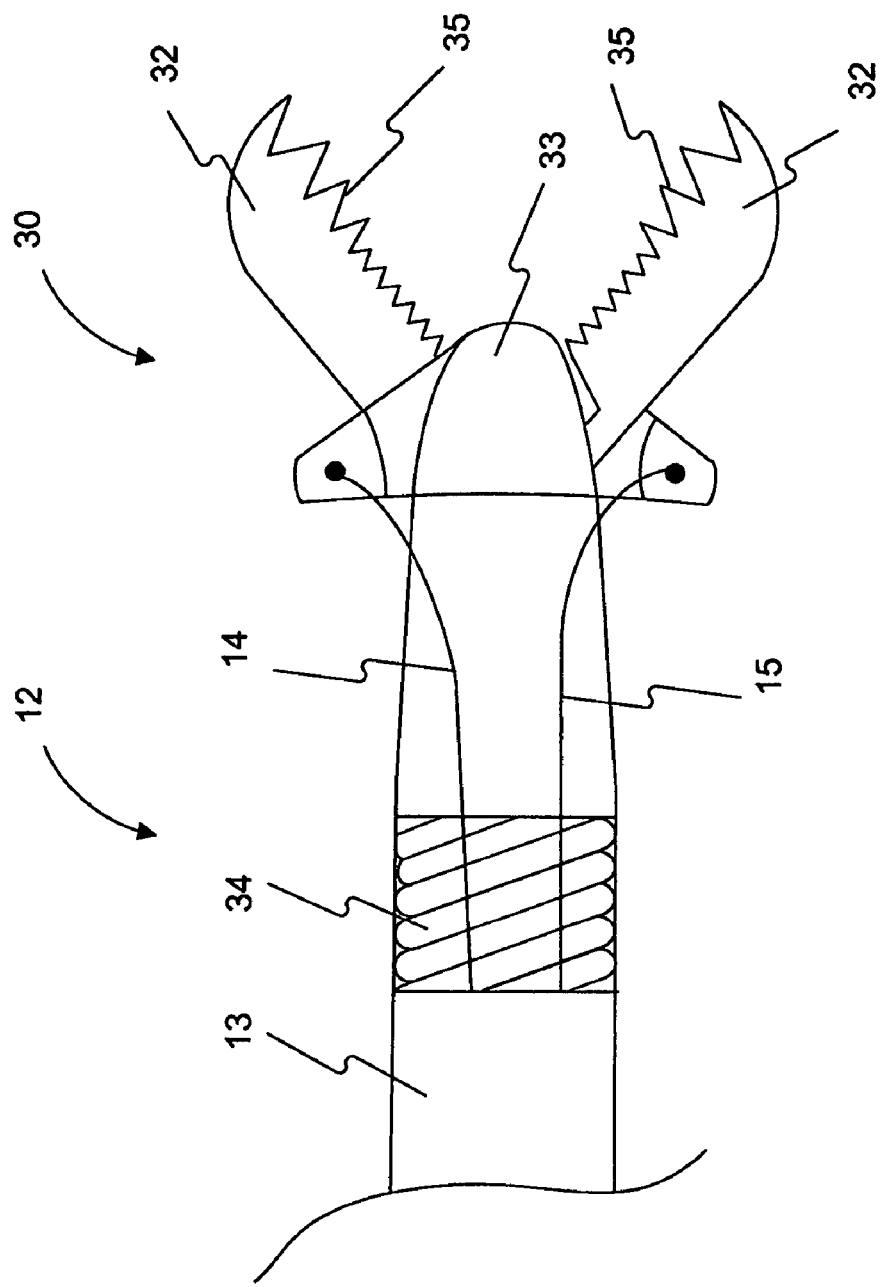
FIG. 2 is a schematic view of an end effector assembly of a medical device.

An exemplary embodiment of a medical device for use with a protective cap is depicted in FIG. 1. The medical device is an endoscopic instrument 10 that includes a handle portion 11 and an end effector assembly 12 connected to each other by a flexible elongate member 13. Control wires 14, 15 extend between the handle portion 11 and the end effector assembly 12 via a lumen in the flexible elongate member 13. The handle portion 11 includes an elongate portion 16 connected at its proximal end to a ring portion 17. A spool portion 18 is slidably disposed around the elongate portion 16. A part of the handle portion 11, for example, the spool portion 18, may be connected to a hypotube 22 which in turn may be connected to the control wires 14, 15. The elongate member 13 may have a coiled portion 34 along all or part of its length, as shown in FIG. 2. The control wires 14, 15 may be connected at their distal ends to opposing portions of the end effector assembly 12, and at their proximal ends to hypotube 22. Due to the connection between the spool portion 18, the hypotube 22, wires 14, 15, and end effector assembly 12, longitudinal movement of the spool portion 18 relative to the elongate portion 16 causes the actuation of the end effector assembly 12 via the control wires 14, 15.

The end effector assembly 12 may be a biopsy forceps jaw assembly 30. The biopsy forceps jaw assembly 30, such as that shown in FIG. 2, includes a pair of jaws 32 disposed between a clevis 33, the clevis 33 being connected to the coiled portion 34 of the member 13. The jaws 32 are pivotally attached to the clevis 33 and pivot relative to one another. One of the control wires 14, 15 attaches to a proximal end of each jaw 32. Each jaw 32 includes a sharp edge or teeth 35 forming a cutting edge. The cutting edge is sharp to cut tissue and obtain tissue samples for evaluation.

FIGS. 1 and 2 show an exemplary medical device for use in connection with a cap according to the invention. Other medical endoscopic devices and non-endoscopic devices, having other distal assemblies may be used with a cap. Though embodiments of the cap will be described in connection with the device 10 of FIGS. 1 and 2, the invention is not limited by the type of medical device.

An exemplary embodiment of a cap that may be placed on the end effector assembly 12, for example jaw assembly 30, is depicted in FIGS. 3 and 4. The cap 100 may include a main body 101 with one or more cavities 102 configured to receive, retain, and protect at least a portion of the end effector assembly 12 (e.g., the jaws 32, and/or the clevis 33). Cavity 102 may be sufficiently long to also receive a portion of the member 13. The cap 100 may protect the end effector assembly 12, for example, so as to prevent damage to portions of the end effector assembly 12 (e.g., jaws 30, teeth 35) during transport, handling, and/or setup. The cap 100 may also prevent portions of the end effector assembly 12, for example the teeth 35, from getting caught on and/or damaging external objects (e.g., packaging, a user) during manufacturing, transport, handling, and/or setup of the device. The cap 100 also reduces the amount of packaging and/or materials necessary to protect the end effector assembly 12.

The outer surface 104 of the main body 101 may be configured to assist the user in holding and/or manipulating the cap 100. The outer surface 104 of the main body 101 may be configured (e.g., sized, contoured, and/or textured) to be ergonomically comfortable as the cap 100 is handled by the user. For example, the outer surface 104 may have a groove (e.g., a concave circular shape) configured to assist the user in gripping the main body 101 of the cap 100. The outer surface 104 may have a larger circumference at its proximal end than at its distal end, for example, to make it easier for the user to place the cap 100 on the end effector assembly 12.

Portions of the main body 101 and cavity 102 may be configured to receive and retain at least a portion of the end effector assembly 12 within the cavity 102. For example, at least a portion of the side surface 103 of the cavity 102 may have a diameter slightly smaller than an outer diameter of the end effector assembly 12 and/or member 13 so as to be configured to form a press fit with at least a portion of the outer surface of the end effector assembly 12 and/or member 13. The cavity 102 may have a volume that is substantially the same as the volume of at least the part of the end effector assembly 12 and/or member to be placed in the cavity 102. The cavity 102 may be sized such that the cap 100 will remain on the end effector assembly 12 despite minor handling and/or jostling. At least the portion of the main body 101 defining cavity 102 may be made of a flexible, elastomeric, and/or otherwise suitable material configured to assist in receiving and retaining the end effector assembly 12, for example, silicone, rubber, plastic, polyurethane, polymer(s), or any other suitable material known in the art. In some embodiments, the main body 101 may be made of a hard polymer and/or metal, and the cap 100 may be attached to the end effector assembly 12 using a suitable fastener such as one or more clips, snaps, and/or flexible inserts.

The cap 100 may also include one or more shafts 110 configured to assist the user in removing tissue and/or any other soft object, for example from the interior portion of a jaw 32, without damaging or otherwise compromising the integrity of the tissue. Such removal of the tissue without damage may be desirable, for example, so that the tissue may be subsequently analyzed.

The shaft 110 may be connected at its proximal end 111 to the main body 101 by any method known in the art. For example, the shaft 110 may be integrally formed with the main body 101 or the shaft 110 may be affixed to the main body 101 using an adhesive. The shaft 110 may be made of any suitable material known in the art having sufficient rigidity to accomplish tissue removal, and may be made out of the same material as the rest of the cap 100 as set forth above.

The distal end 112 of the shaft 110 may be configured to remove tissue and/or any other soft object that may be disposed in the interior portion of the biopsy forceps jaw assembly 30. The distal end 112 may also be configured so as to allow the user to remove the tissue from the jaw assembly 30 without damaging or otherwise compromising the integrity of the tissue (e.g., for pathological analysis or other purposes) or components of the jaw assembly 30. For example, the distal end 112 may be tapered to a tip. The tip may be sharp enough to pierce tissue and/or be made of a material that is rigid enough to pierce tissue. In FIG. 3, only a portion of the shaft 110 may be tapered, however, FIG. 6 depicts an embodiment where substantially the entire shaft 120 uniformly tapers around the axis of the shaft 120 from its proximal end 121 to its distal end 122.

The distal end 112 may also be configured to not injure the user. This aspect of the invention, along with the fact that the shaft 110, 120 is disposed on the cap 100, reduces the risk that the user will be inadvertently stuck with a needle, toothpick, or another ancillary device while the user is using that ancillary device to remove the tissue from the end effector assembly 12, jaw assembly 30, and/or jaws 32. Indeed, the cap 100 eliminates the necessity of using a needle, toothpick, or another ancillary device to remove the tissue.

The shaft 110 may be configured to both remove tissue and/or any other soft object that may be disposed in the interior portion of the biopsy forceps jaw assembly 30 and to not injure the user. For example, the shaft 110 may be made of a material having a durometer that is chosen so that there is a balance between rigidity and flexibility. The shaft 110 may, at the same time, be rigid so as to be effective in removing tissue, and yet be flexible enough so as to decrease the potential for injuring tissue, the user, and/or packaging. In another example, the shaft 110, including the distal end 112 of the shaft 110, may have a shape and/or design that decreases the likelihood that the shaft 110 will damage tissue, the user, and/or packaging. Indeed, the shaft 110 may be made of a material and have a design configured so as to allow the shaft 110 to both remove tissue and/or any other soft object that may be disposed in the interior portion of the biopsy forceps jaw assembly 30 and not injure the user.

As depicted in the embodiment shown in FIG. 5, the cap 200 may include a protrusion or disk 230 substantially disposed around the shaft 210 and/or main body 201. The disk 230 may have a substantially circular shape or any other desired shape. At least a portion of the disk 230 may extend beyond the outermost radial portion of the shaft 210 and/or main body 201. The disk 230 may be integrally formed with the shaft 210 and/or main body 201, or the disk 230 may be a separate component fixedly placed on the shaft 210 and/or main body 201. When placed on the shaft 210 and/or main body 201, the disk 230 may form a press-fit with at least a portion of the shaft 210 and/or main body 201 or may be adhered through any other suitable method. Disk 230 aids in insertion of cap 200 over, and removal from, an end effector assembly. In addition, the disk 230 may be configured to prevent the cap 200 from being placed inside a working channel of an endoscope, for example, by having a width and/or cross-section greater than the width and/or cross-section of the working channel of the endoscope. This may be desirable so as to prevent the cap 200 from becoming lodged in the working channel of the endoscope and/or body cavity. By eliminating the possibility of the cap 200 becoming lodged in the working channel of the endoscope, there is no need to spend time and/or energy removing the cap 200 from the working channel. Accordingly, the procedural efficiency of endoscopic procedures is increased. Main body 101 of cap 100 may be similarly sized to prevent introduction of cap 100 into an endoscope channel.

Figure 8A:
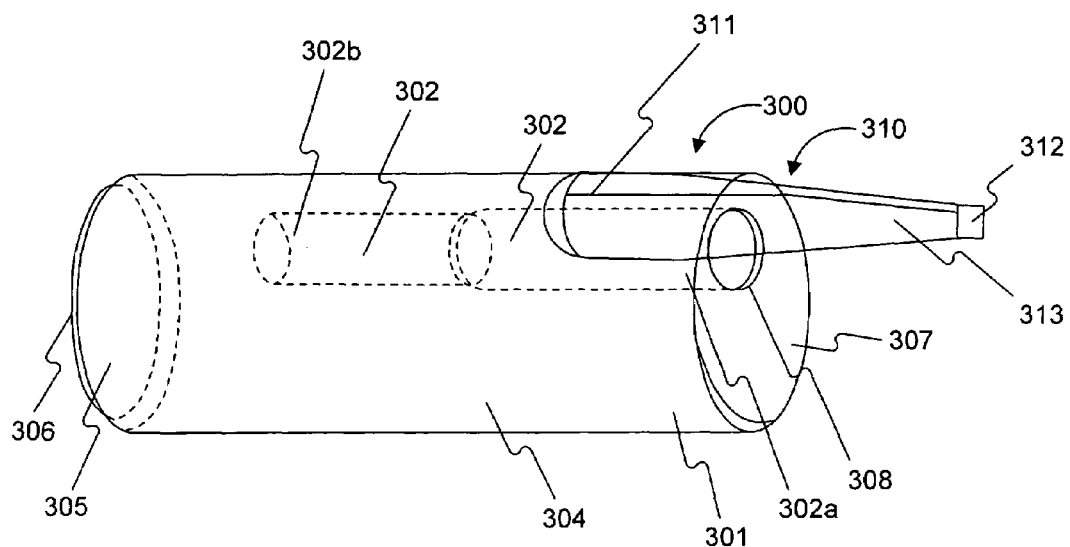
FIGS. 8A-8B are schematic views of a protective cap according to yet another embodiment of the present invention.
Figure 8B:
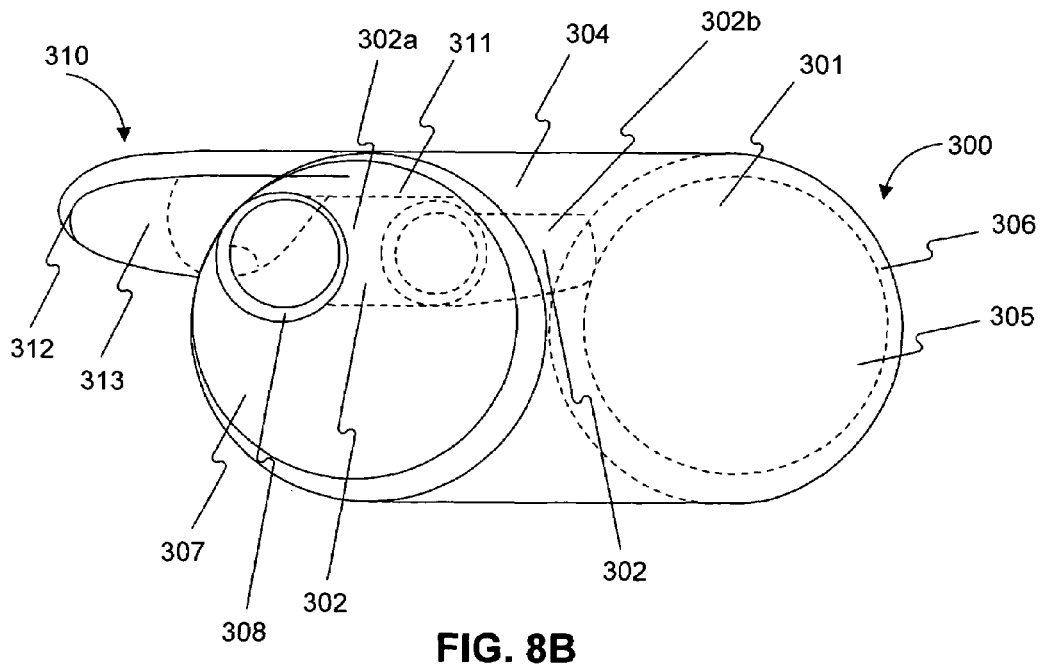

FIGS. 8A-8B depict another exemplary embodiment of the invention. FIGS. 8A-8B depict a cap 300 having a main body 301 defining a cavity 302. A shaft 310 may extend from the main body 301.

The main body 301 may have a configuration similar to any main body 101, 201 disclosed herein. The main body 301 may define an outer surface 304 configured to allow a user to grip, handle, and/or transport the cap 300.

Figure 9A:
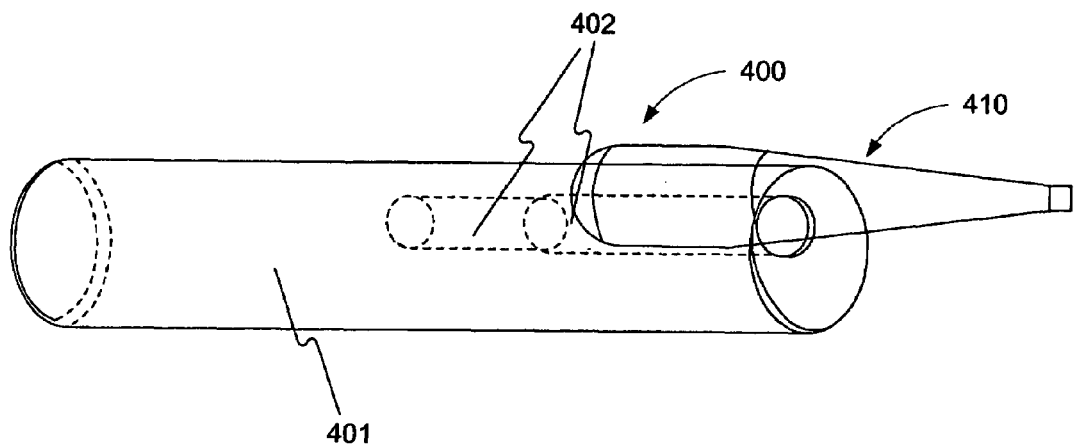
FIGS. 9A-9B are schematic views of a protective cap according to a yet further embodiment of the present invention.
Figure 9B:
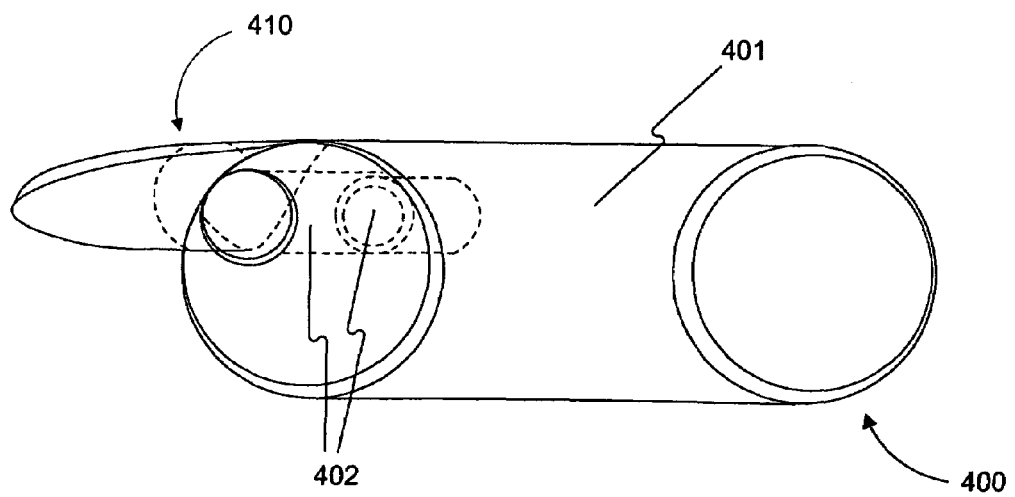

The main body 301 may have any suitable shape, dimensions, and/or configuration. For example, the main body 301 of cap 300 may have a substantially cylindrical shape. In another example, the main body 301 of cap 300 may be shorter in length than the main body 401 of a cap 400 which is shown in FIGS. 9A-9B. A longer length for main body 401 may be desirable to allow the user to more easily grasp and/or retain the cap 400, or to permit a greater length of the distal portion of a medical device to insert into a cavity 402 of the cap 400.

Figure 10A:
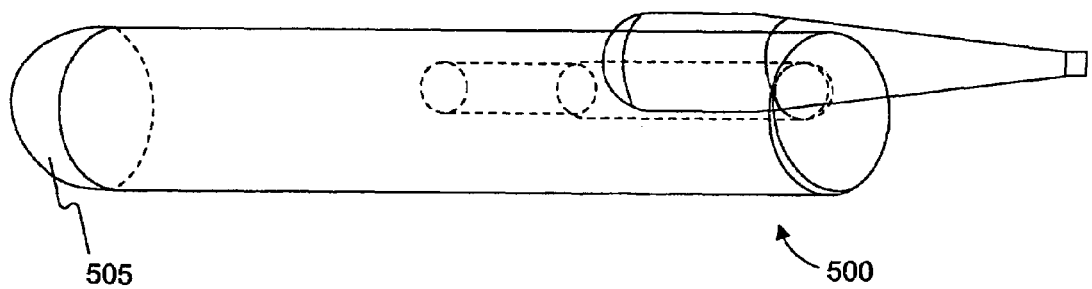
FIGS. 10A-10B are schematic views of a protective cap according to still another embodiment of the present invention.
Figure 10B:
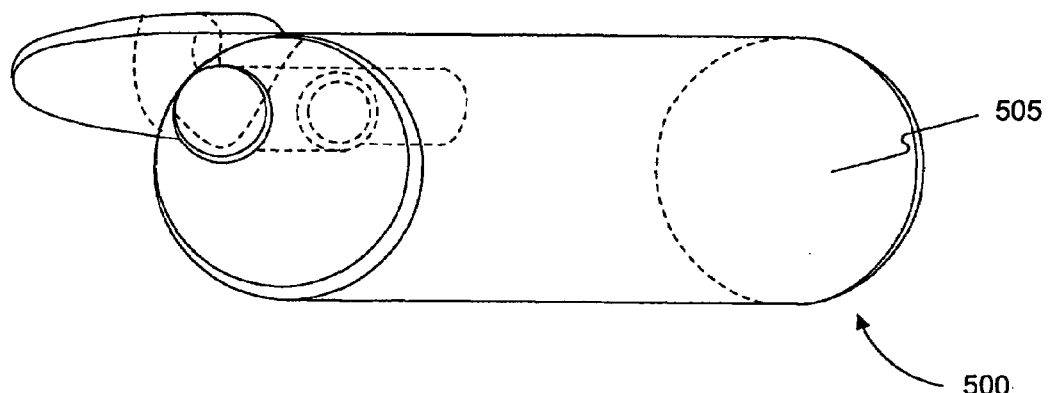

A distal end 305 of the cap 300 may have any suitable shape, dimensions, and/or configuration. For example, the distal end 305 of the main body 301 may have a substantially flat configuration, and the edge 306 of distal end 305 that is adjacent to outer surface 304 may be chamfered. In another example, a distal end 505 of a main body 500, as shown in FIGS. 10A-10B, may have a substantially hemispherical shape. A chamfered edge 306 and/or a hemispherical distal end 505 may be desirable, for example, to prevent the distal end 305, 505 and/or edge 306 from injuring the user and/or puncturing the packaging within which the cap 300, 500 may be disposed.

Figure 11A:
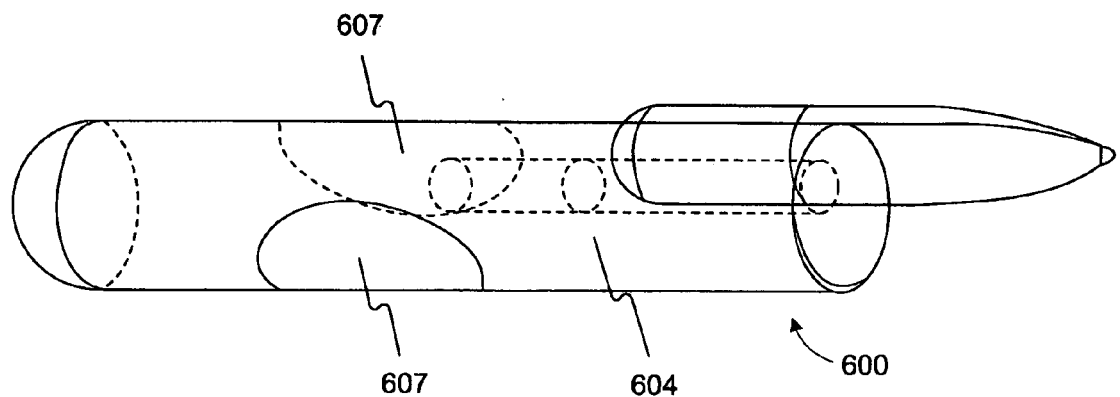
FIGS. 11A-11B are schematic views of a protective cap according to a still further embodiment of the present invention.
Figure 11B:
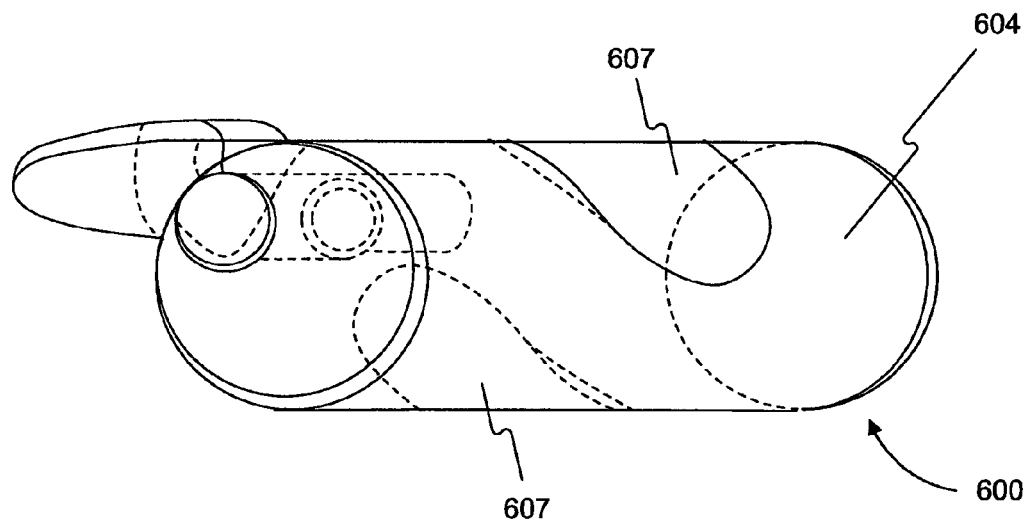

The outer surface 304 of the cap 300 may have any suitable shape, dimensions, and/or configuration. For example, the outer surface 304 may have a substantially cylindrical shape and/or be substantially smooth. In another example, an outer surface 604 of a cap 600, as shown in FIGS. 11A-11B, may have one or more grooves 607. The grooves 607 may have any suitable shape, dimensions, texture, and/or configuration. For example, the grooves 607 may be configured to allow a user to more easily grip and/or handle the cap 600. In another example, the grooves 607 may be sized so as to allow a user's fingers to comfortably fit within the grooves 607. In a further example, the grooves 607 may be disposed on any portion of the outer surface 604 of the cap 600. In FIGS. 11A-11B, the grooves 607 are disposed on substantially opposite sides of the cap 600. One or more grooves 607 may be configured such that they form one or more knurls on the outer surface 604. The outer surface 304 may be configured to prevent the outer surface 304 of shaft 310 from injuring the user and/or damaging the packaging. For example, the outer surface 304 may be substantially smooth and/or have substantially chamfered or rounded edges.

Cavity 302 may have a configuration substantially similar to cavity 102. Cavity 302 may include subcavities 302a and 302b. Subcavity 302a may extend from a proximal surface 307 of cap 300 and may have a substantially cylindrical shape. An edge 308 where subcavity 302a meets proximal surface 307 of cap 300 may be chamfered, for example, for ease of entry of end effect in assembly 12 into sub cavity 302a and to prevent damage to the end effector assembly 12, as the end effector assembly 12 is placed within the cavity 302. Subcavity 302b may be adjacent to and/or in flow communication with subcavity 302a. Subcavity 302b may be disposed distally from proximal surface 307 and/or subcavity 302a. Subcavity 302b may have a configuration substantially similar to and/or different from subcavity 302a. Subcavity 302b may be substantially cylindrical in shape and/or have a cross-sectional area smaller than subcavity 302a. Subcavity 302b may have a configuration different from subcavity 302a, for example, to accommodate end effector assemblies having different sizes and/or to accommodate an end effector assembly having multiple portions having different sizes; Cavity 302 may extend any suitable depth within main body 301. For example, cavity 302 may extend through most of the main body 301. In another example, cavity 402 may extend through less than half of the main body 401, as shown in FIGS. 9A-9B.

Shaft 310 may be configured to assist the user in removing tissue samples from the inner portions of forceps 32. A distal end 311 of shaft 310 may extend from a portion of the outer surface 304 of the main body 301 and extend proximally past the proximal surface 307 of the main body 301. However, the shaft 310 may extend and/or be disposed on any portion of main body 301. A portion of the shaft 310 adjacent the main body 301 may be rounded, for example, to reduce the likelihood of injuring a user and/or damaging external objects (e.g., packaging).

Shaft 310 may have any suitable shape, dimensions, and/or configuration. Shaft 310 may taper towards proximal end 312. However, shaft 310 may extend in any direction from main body 301. Proximal end 312 may include a sharp or dull tip. As shown in FIGS. 9A-9B, a shaft 410 may be longer than shaft 310. Such a longer shaft 410 may be desirable, for example, to more easily remove tissue from deeper forceps 32. Shaft 310 may have a substantially triangle shaped cross-section. Shaft 310 may be made out of any suitable material, for example, any material set forth herein.

Figure 13:
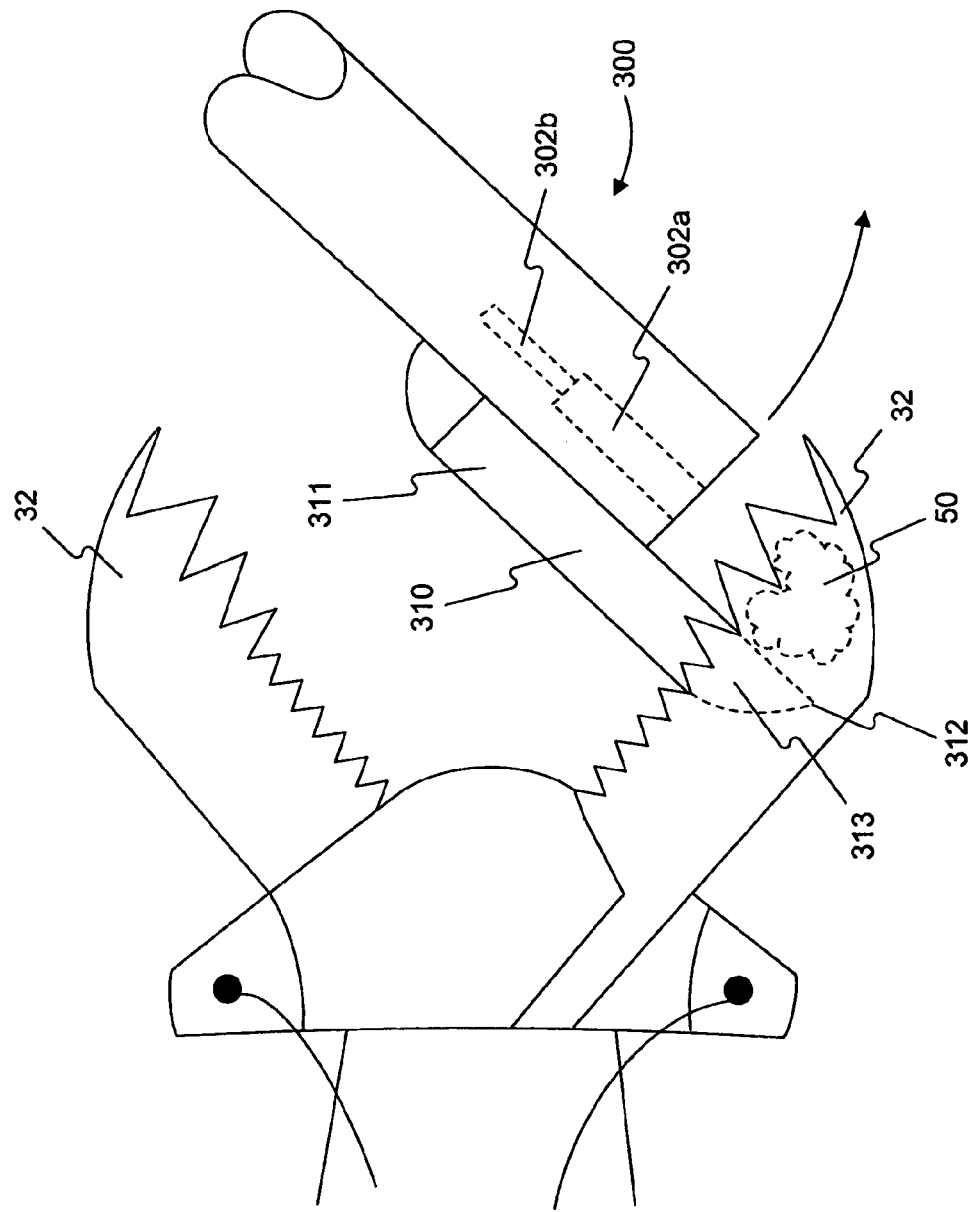
FIG. 13 is a schematic view of a method of using the protective cap of FIGS. 8A-8B.

An inner portion 313 of shaft 310 may have a concave surface. Accordingly, shaft 310 may be relatively thin. The inner portion 313 may be concave, for example, to assist the user in removing tissue 50 from the inner portion of the forceps 32. Inner portion 313 may allow a user to scoop tissue 50 out of the inner portion of the forceps 32. An example of scooping tissue 50 using shaft 310 is shown in FIG. 13, wherein the shaft 310 may be moved in the direction of the arrow.

Figure 12:
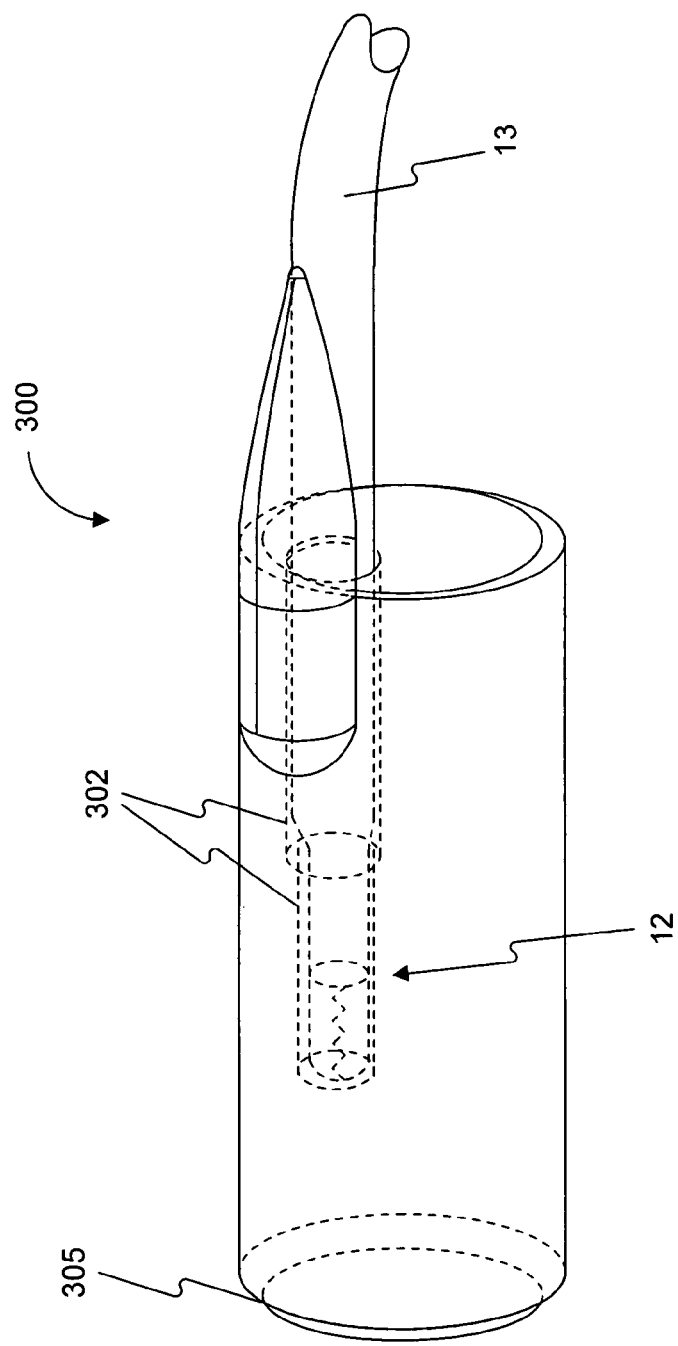
FIG. 12 is a schematic view of the protective cap of FIGS. 8A-8B covering the end effector assembly of a medical device.

As shown in FIG. 12, when end effector assembly 12 is disposed within cavity 302 of cap 300, the cap 300 is configured so as to reduce the likelihood that the shaft 310 may injure the user and/or damage the packaging. This is because shaft 310 extends proximally away from distal end 305 and may be substantially adjacent a portion of the end effector assembly 12 and/or elongate member 13.

A cap according to any embodiment, and/or any portion thereof, may be manufactured using any suitable method known in the art. For example, the cap and/or any portion thereof may be injection molded, milled, stamped, and/or pressed out of any suitable desired material known in the art.

In an exemplary method of using a cap of the invention, the cap 100 may be placed around at least a portion of an end effector assembly 12. The fit between the cap 100 and end effector assembly 12 may be snug enough so as to prevent the cap 100 from becoming inadvertently dislodged during transport and/or handling prior to the use of the medical device 10. With such a cap 100 in place on the assembly 12, minimal further packaging may be necessary for the transportation and/or storage of the device 10, minimizing the amount of waste from packaging.

Once the user unpacks device 10 from its packaging and intends to use device 10, the user may remove the cap 100 from the end effector assembly 12. Should the user forget to remove the cap 100 from the end effector assembly 12, and attempt to place the end effector assembly 12 down the working channel of the endoscope with the cap 100, the main body 101 on the cap 100 (or disk 230 on cap 200) may prevent the user from placing the cap 100 and end effector assembly 12 down the working channel of the endoscope.

Figure 7:
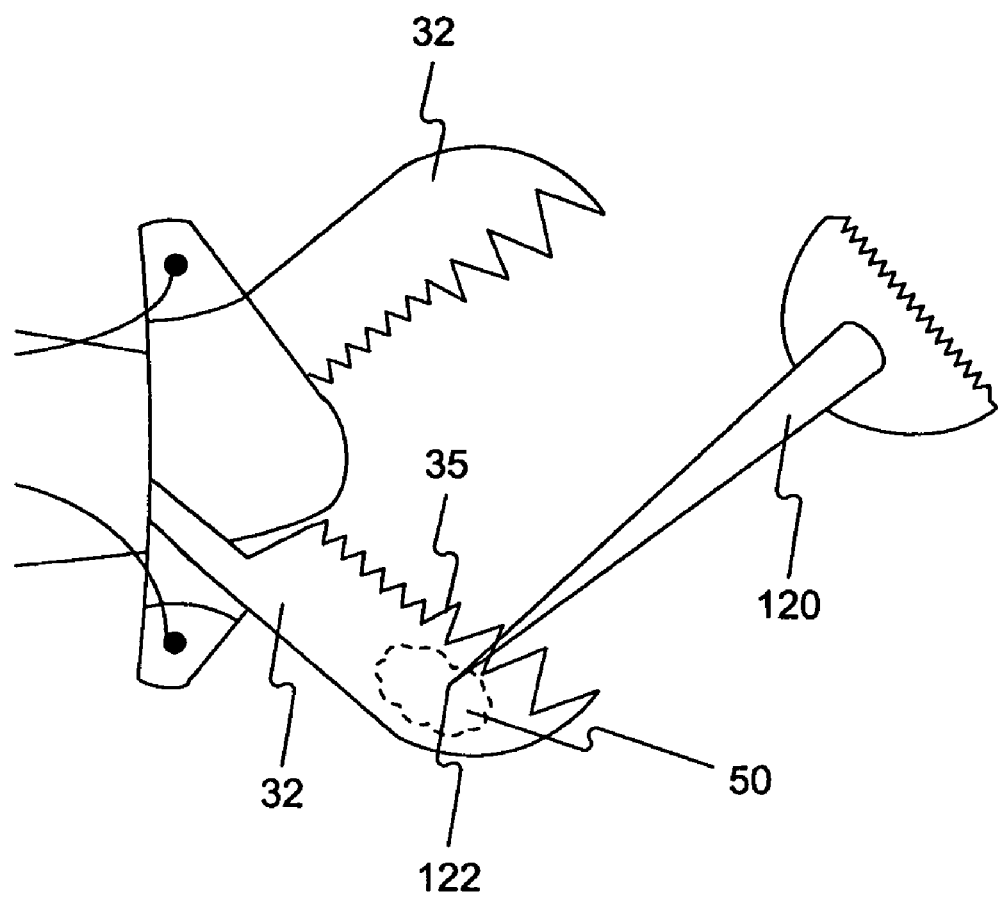
FIG. 7 is a schematic view of a method of using the protective cap of FIG. 6.

Once the cap 100 has been removed from the end effector assembly 12, the end effector assembly 12 may be placed into a body cavity and used to acquire a tissue sample 50. The end effector assembly 12 may then be removed from the body cavity, and, as shown in FIG. 7, the tissue sample 50 may be removed from the interior of the assembly 12 using the distal end 112, 122 of the shaft 110, 120 of the cap 100. The assembly 12 may then be reinserted into the body cavity to acquire another tissue sample, for example, without placing the assembly 12 in formalin.

In various embodiments, all aspects of the invention set forth herein may be used in conjunction with any medical device, instrument, or procedure, and/or any non-medical device, instrument, or procedure. In addition, any aspect of the invention set forth herein may be used in conjunction with or separate from any other aspect of the invention set forth herein.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of performing a medical procedure, comprising:
   providing a medical device including a handle portion, an end effector assembly, and an elongate member connecting the handle portion to the end effector assembly;
   providing a cap including a body defining a cavity configured to accommodate at least a portion of the end effector assembly of the medical device, and a tissue removal portion attached to the body and configured to remove a tissue sample disposed within the end effector assembly when the cavity is not accommodating the end effector assembly, at least a portion of the end effector assembly being disposed in the cavity;
   removing the cap from the at least a portion of the end effector assembly;
   obtaining tissue with the end effector assembly; and
   removing tissue from the end effector assembly with the tissue removal portion.

2. The method of claim 1, wherein the end effector assembly is a jaw assembly.

3. The method of claim 1, wherein the medical device is a endoscopic biopsy forceps.

4. The method of claim 1, wherein the at least a portion of the end effector assembly is disposed in the cavity when the end effector assembly is in a closed configuration.

5. The method of claim 1, wherein the tissue removal portion is a shaft.

6. The method of claim 5, wherein the shaft is tapered to a tip.

7. The method of claim 1, wherein the body includes a concave outer surface.

8. The method of claim 1, wherein at least a portion of the cap is made of an elastomeric material.

9. The method of claim 1, further comprising a protrusion radially extending beyond an outermost radial portion of the body and the tissue removal portion.

10. The method of claim 9, wherein the protrusion is a disk.

11. The method of claim 9, wherein the protrusion has a greater cross-sectional area than the body.

12. The method of claim 1, further comprising a protrusion configured to prevent the cap from advancing through a working channel of an endoscope.

13. The method of claim 1, wherein the tissue removal portion is integrally formed with the body.

14. The method of claim 1, wherein the tissue removal portion is configured to scoop tissue out of the end effector assembly.

15. The method of claim 1, wherein the tissue removal portion includes a concave inner surface.

16. The method of claim 1, wherein the tissue removal portion is configured to extend alongside the end effector assembly when the cavity is accommodating the end effector assembly.

17. The method of claim 1, wherein the tissue removal portion extends from an end of the body that defines an opening of the cavity.

18. The method of claim 1, wherein the tissue removal portion extends from a first end of the body opposite a second end of the body that defines an opening of the cavity.

19. The method of claim 1, further comprising scooping tissue out of the end effector assembly with the tissue removal portion.

* * * * *